United States Patent

Backlund et al.

[11] Patent Number: 5,869,774
[45] Date of Patent: Feb. 9, 1999

[54] DEVICE FOR TAKING A LIQUID SAMPLE

[75] Inventors: Ulf Backlund, Stockholm; Urban Ungerstedt, Lindingö, both of Sweden

[73] Assignee: CMA/Microdialysis AB, Solna, Sweden

[21] Appl. No.: 809,084

[22] PCT Filed: Sep. 14, 1995

[86] PCT No.: PCT/SE95/01039

§ 371 Date: Apr. 9, 1997

§ 102(e) Date: Apr. 9, 1997

[87] PCT Pub. No.: WO90/08726

PCT Pub. Date: Mar. 21, 1996

[30] Foreign Application Priority Data

Sep. 14, 1994 [SE] Sweden .................................. 9403072

[51] Int. Cl.⁶ .......................... G01N 35/08; F04B 43/12; F04B 41/06
[52] U.S. Cl. ..................... 73/864.34; 73/864.12; 73/864.22; 417/199.1; 417/477.1
[58] Field of Search .......................... 73/864.34, 864.35, 73/864.14, 864.22, 864.12; 417/199.1, 474, 476, 477.1, 477.6, 477.13

[56] References Cited

U.S. PATENT DOCUMENTS

| | | |
|---|---|---|
| 1,845,479 | 2/1932 | Carpenter ............................ 417/476 X |
| 3,306,229 | 2/1967 | Smythe . |
| 3,572,998 | 3/1971 | Anthon .............................. 73/864.22 X |
| 3,614,434 | 10/1971 | Horwitz et al. .................. 73/864.22 X |
| 3,654,959 | 4/1972 | Kassel ...................... 137/605 |
| 3,994,687 | 11/1976 | Englebrecht ..................... 73/864.22 X |
| 4,413,534 | 11/1983 | Tomoff et al. ................... 73/864.22 X |
| 4,528,158 | 7/1985 | Gilles et al. ..................... 73/864.22 X |
| 4,660,607 | 4/1987 | Griffith et al. .................. 417/477.1 X |
| 5,356,267 | 10/1994 | Fulmer ............................. 417/477.1 X |
| 5,474,744 | 12/1995 | Lerch .................................. 73/864.22 |

FOREIGN PATENT DOCUMENTS

| | | |
|---|---|---|
| 43487 | 4/1977 | Japan ................................ 73/864.22 |
| 9585 | 3/1986 | Japan ................................ 73/864.22 |
| 227629 | 9/1990 | Japan ................................ 73/864.34 |
| 37 794 | 10/1974 | Sweden . |
| 1 502 677 | 3/1978 | United Kingdom . |
| 2 085 161 | 4/1982 | United Kingdom . |
| WO 93/12432 | 6/1993 | WIPO . |

*Primary Examiner*—Thomas P. Noland
*Attorney, Agent, or Firm*—Young & Thompson

[57] ABSTRACT

Apparatus for taking up liquid batches, comprising a take-up tube (10), a metering pump (20) for drawing liquid into the take-up tube by suction, and a washing pump (30) which functions to pump washing solution through the take-up tube in a direction opposite to the liquid take-up direction, through the medium of a washing tube (50). The washing pump is a self-sealing displacement pump.

5 Claims, 2 Drawing Sheets

DEVICE FOR TAKING A LIQUID SAMPLE

FIELD OF THE INVENTION

The present invention relates to apparatus for taking-up liquid batch-wise, said apparatus including a take-up tube, a metering pump for drawing liquid into the tube by suction, and a washing pump arranged to pump washing solution through the take-up tube in a direction opposite to that in which the liquid is taken-up, through the medium of a washing tube.

BACKGROUND OF THE INVENTION

Many different types of apparatus of this kind are known within the art. Pipetting apparatus and other types of apparatus for laboratory and/or clinical use, for instance dosing or metering devices for different types of analytic apparatus, will often comprise an arrangement which includes a dosing pump for taking different samples and reagents, and a washing pump which is used to wash away sample and reagent residues from the apparatus upon completion of the pipetting or analysis process. The washing pump is typically a plunger-operated pump or a syringe pump. A valve is required for connection of the washing tube when taking-up liquid, and correspondingly a valve is required for closing the take-up tube when pumping-up washing solution. In some cases, it has been possible to simplify the apparatus slightly, by using only one valve, in the form of a two-port two-position valve, which in one position connects the washing pump to a washing solution container, thus for taking-up washing solution, and in its other position connects the washing pump to the dosing pump and the take-up tube so that they can be washed with the washing solution.

An example of such an arrangement is described, for instance, in WO 93/12432. This publication describes an arrangement for washing a probe used in an analytic system. In the case of this known arrangement, the probe is washed with liquid and compressed-air or in some corresponding fashion in a reverse direction, i.e. liquid is passed to a two-way valve with the aid of a syringe pump, said valve being controlled to allow a mixture of liquid and compressed-air to pass through to the probe and therewith wash the same.

In addition to this type of arrangement being complicated by valves and valve control systems, the problem remains that the wash capacity of the washing pump is naturally restricted to the volume of washing solution that can be drawn up by the pump in one working stroke. Although it is feasible to suck-up and inject washing solution repeatedly during a washing process, such a procedure is particularly time-consuming.

Another solution to the problem is described in the British Patent Specification GB 1,502,77. This publication describes a device for taking-up and analyzing a liquid in which a peristaltic pump is used to move liquid through the device. By liquid is meant here the sample, possible reagent and washing solution. In the case of this device, the sampling probe is submerged into washing liquid which is taken-up through the probe orifice so as to wash the device. The sample and the washing solution thus pass through the device in one and the same direction and through one and the same pump, which places high demands on adequate washing of the device, among other things. The use of the peristaltic pump to take-up samples means that the amounts of sample that can be taken are greatly dependent on the specific construction of the pump.

OBJECTS OF THE INVENTION

One object of the invention is to provide effective and positive cleaning apparatus.

A further object of the invention is to provide simple and functionally reliable cleaning apparatus.

Another object of the invention is to control the amount of sample taken in a positive and repeatable manner.

It will be apparent from the following description that these objects are realized with the inventive apparatus.

SUMMARY OF THE INVENTION

It has been possible to solve the aforesaid problems in a very simple manner, by using a self-sealing displacement pump as the washing pump in accordance with the present invention. The self-sealing displacement pump functions as a valve in itself when static. Because a pump of this kind is able to draw up washing solution continuously when in operation, the washing capacity of the pump is restricted only by the amount of washing solution that is available.

The inventive apparatus has also shown itself to be advantageous from a production/technical aspect, since the apparatus can be manufactured more easily than known apparatus of a similar nature and because the novel apparatus is comprised of a relatively few components of standard design.

By "self-sealing displacement pump" is meant in this document pumps which, in operation, force enclosed volumes of liquid to move in the pumping direction and force or pump volumes of liquid through the pump outlet in a uniform and continuous flow, without the aid of separate valves to this end. Multidisc pumps and peristaltic pumps are examples of such self-sealing displacement pumps.

In the case of one preferred embodiment of the present invention, the self-sealing displacement pump is a peristaltic pump, i.e. a displacement pump with which liquid is pumped by periodically squeezing together an elastically deformable tube with the aid of a system of tube-squeezing devices which act in the pumping direction. For instance, a peristaltic pump can be said to include a rotatable disc in the form of a pump wheel having a number of rollers mounted around its periphery and projecting out so as to be able to press against an elastically deformable tube, in this case the washing tube.

In one particularly preferred embodiment of the present invention, the rollers of the peristaltic pump are intended to be located in at least one predetermined position when the pump is static. By this is meant that the rollers are able to stop only at certain specific positions but that an individual roller can be located in any one of these positions whatsoever. For instance, if the pump has five rollers, each roller is able to stop in one of five specific positions, and in one of six specific positions when the pump has six rollers, and so on. The purpose of this embodiment is to enable very small volumes of liquid to be taken-up reproducibly and with great precision with the aid of the dosing pump. The roller that closes the flexible tube nearest the dosing pump must stop at a specific position in order for the length of the flexible washing tube between the washing pump and the dosing pump not to vary from one fluid or liquid take-up to another. The flexible washing tube, or at least that part of the tube on which the peristaltic pump acts, is elastically deformable, meaning that at least a part of said tube length will be compressed when sucking-up liquid with the aid of the dosing pump and therewith that part of the content of said tube length will flow into the dosing pump and influence its take-up volume. In order to obtain reproducible take-up with the greatest possible precision, this influence must be essentially of equal magnitude from one pumping sequence to another, which means, in turn, that the length of washing tube between the washing pump and the dosing pump must not, in principle, vary between pumping sequences.

BRIEF DESCRIPTION OF THE DRAWINGS

The present invention will now be described in more detail with reference to exemplifying embodiments thereof and also with reference to the accompanying drawings, in which.

DETAILED DESCRIPTION OF THE INVENTION

Figure 1:
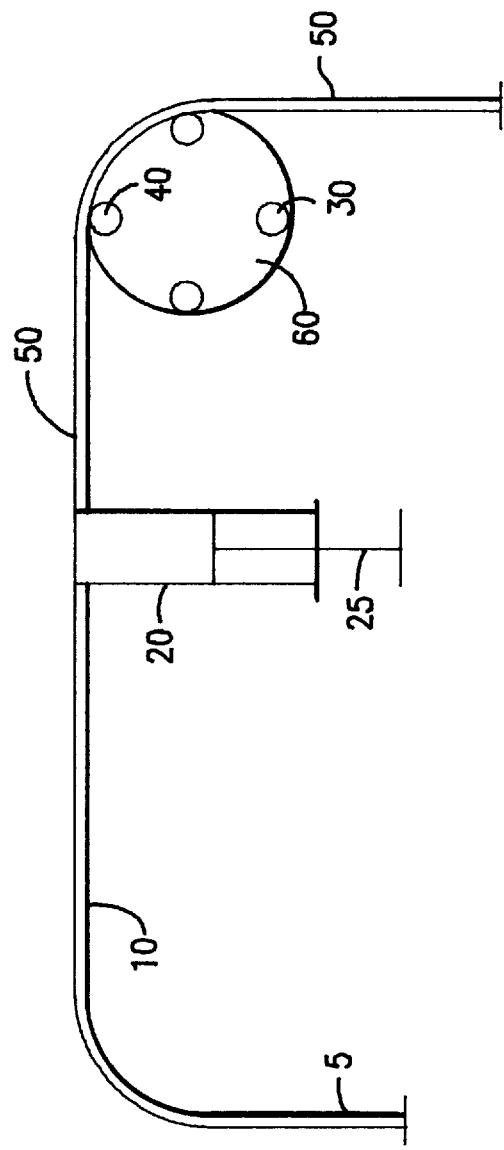
FIG. 1 is a schematic illustration of apparatus constructed in accordance with one embodiment of the present invention.

The apparatus shown in FIG. 1 includes a flexible take-up tube 10 having an outer tube-end 5, a dosing pump 20, a washing pump 30 and a flexible washing tube 50. When the apparatus is at rest, the tube 10, the dosing pump 20, the washing pump 30 and the washing tube 50 are all full of washing solution. When the apparatus is to be used, a small quantity of air is first pumped into a device (not shown) connected to the tube-end 5. The device may have the form of a pipette or an automatic sample injector belonging to an HPLC-apparatus. The air is drawn into the device with the aid of the dosing pump 20, which in this case is a syringe pump, by drawing out the plunger 25 of said pump 20 so as to generate a subpressure in the tube 10 and in the washing tube 50. Liquid is then sucked-up in a corresponding manner. The washing pump 30 acting on the washing tube 50 in the form of a peristaltic pump having rollers 40 mounted on a pump wheel 60. Because at least one of the rollers 40 lies against the washing tube 50, which is made of an elastically deformable material, and squeezes the tube together, a seal is obtained against the subpressure generated by the pump 20 therewith enabling air or liquid present in the device connected to said tube-end 5 to be taken-up. After having taken-up the liquid, the liquid can be either pumped out with the aid of the pump 20 or the apparatus immediately washed by drawing washing solution into the washing tube 50 from a washing solution container (not shown) with the aid of the washing pump 30, and pumping said solution to the pump 20, the take-up tube 10 and the pipette or automatic sample injector connected thereto.

Naturally, the aforesaid device (pipette, auto-injector or the like) need not be connected to the end 5 of the tube, but may equally as well be connected at some appropriate position on the tube 10 between the tube-end 5 and the dosing pump 20.

Figure 4:
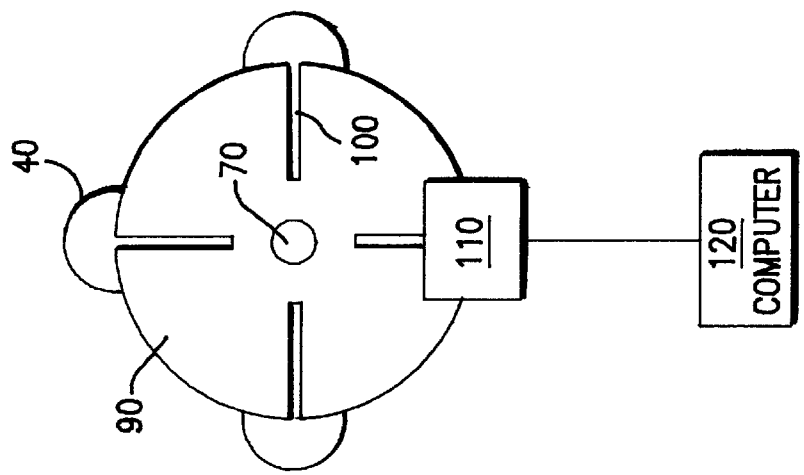
FIG. 4 is an end-view of the arrangement in FIG. 2, as seen from the right in said Figure.
Figure 3:
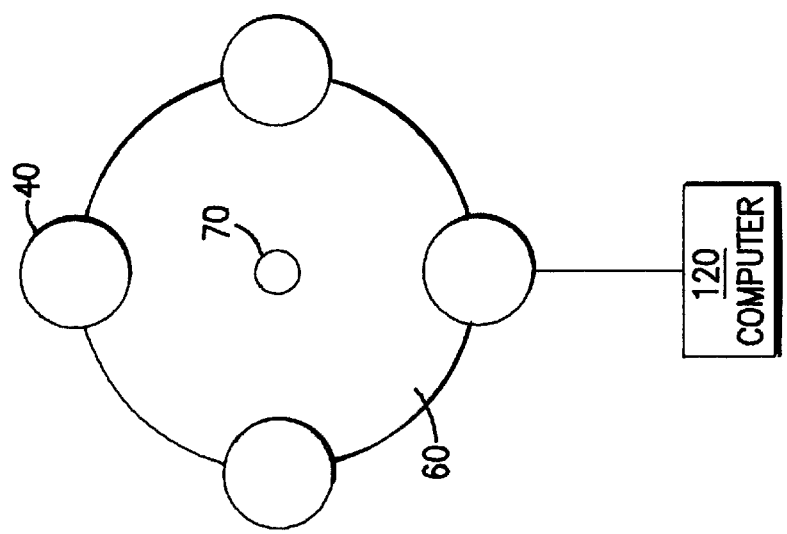
FIG. 3 is an end view of the arrangement shown in FIG. 2 as seen from the left in the Figure.
Figure 2:
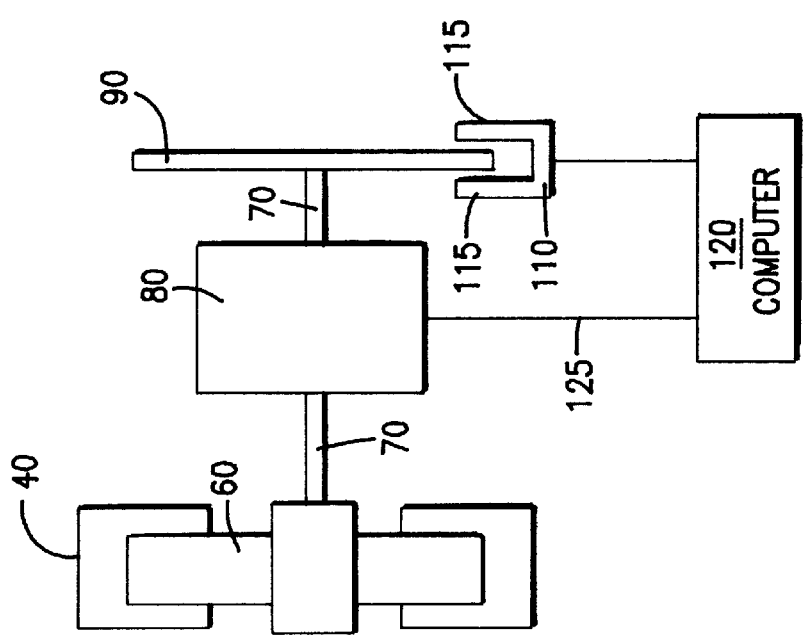
FIG. 2 illustrates a particularly preferred washing pump arrangement in accordance with the invention.

FIGS. 2–4 illustrate the pump wheel 60 of a peristaltic pump which is used as a washing pump in the present apparatus, said pump wheel being provided with four rollers 40. The pump wheel 60 is driven by an electric motor 80 via a shaft 70. In the illustrated case, the electric motor is a stepping motor having product number HY 200-1717 (manufactured by MAE, Milano, Italy). The shaft 70 carries on the other side of the motor 80 a disc 90 which is provided with four slots 100. The positions of the slots 100 on the disc 90 correspond to the positions of the rollers 40 on the pump wheel 60. The disc 90 runs in the gap of a so-called optical reading fork or optobreaker 110, said reading fork being of the kind manufactured by Sharp Corp., Osaka, Japan, and designated GP1A06. The reading fork is connected to a computer 120, which also controls the power supply to the motor 80, through a conductor 125. When the pump is working, the delivery of a requisite volume of washing solution is controlled by the number of revolutions through which the pump wheel 60 rotates. The number of revolution of the pump wheel is, in turn, controlled with the aid of the optobreaker 110, which sends a signal to the computer 120 each time a slot 100 passes between the legs 115 of the optobreaker 110 and light passes from one leg to the other, wherein each signal is added to those signals earlier received by the computer 120. When the number of signals thus produced reaches a given preprogrammed value, i.e. a value which corresponds to the desired number of revolutions of the wheel 60 and therewith the desired volume of washing solution, the computer switches off the power supply to the motor 80 and the wheel 60 and disc 90 respectively stop in a position in which one of the slots 100 is located between the legs 115 of the optobreaker 110.

It will be understood that the invention is not restricted to the aforedescribed and illustrated exemplifying embodiments thereof. For instance, any appropriate detecting means or sensor element, such as a microswitch or Hall element, and discs suitable for use with such detectors or sensor elements can be used instead of the illustrated optical reading fork and slotted disc. Similarly, other components of the illustrated embodiment can be replaced with appropriate alternatives. It will also be understood that the illustrated and described embodiment can be further developed within the scope of the following Claims.

We claim:

1. In an apparatus for taking-up liquid in batches, wherein the apparatus comprises a flexible take-up tube (10), a dosing pump (20) for drawing liquid into the tube (10) by suction, and a washing pump (30) which functions to pump washing solution through the take-up tube (10) in a direction opposite to the liquid take-up direction, through the medium of a flexible washing tube (50); the improvement wherein the take-up tube (10) and the washing tube (50) are connected to one another and form the end parts of a tube system, wherein the dosing pump (20) is placed adjacent the mutually opposing ends of the tubes (10, 50), and wherein the washing pump (30) is a displacement pump which functions to sealingly close the washing tube when the pump is inactive.

2. Apparatus according to claim 1, wherein the displacement pump (30) is a peristaltic pump.

3. Apparatus according to claim 2, wherein the peristaltic pump includes a pump wheel (60) which has at least one roller (40) mounted on the periphery thereof, pump control means being arranged which regulate the setting of the pump wheel (60) so that said at least one roller is located in a predetermined position when the peristaltic pump is not active in pumping washing solution.

4. The use in apparatus for the batch-wise take up of liquid of a displacement pump which sealingly closes a flexible washing tube when the pump is inactive, said apparatus comprising a flexible take-up tube (10), a dosing pump (20) for drawing liquid into the take-up tube (10) by suction, and a washing pump (30) which functions to pump washing solution through the take-up tube (10) in a direction opposite to the take-up direction of the liquid, through the medium of a flexible washing tube (50).

5. The use according to claim 4, wherein the displacement pump is a peristaltic pump.

* * * * *